United States Patent
Lu et al.

(10) Patent No.: US 10,598,563 B2
(45) Date of Patent: Mar. 24, 2020

(54) DOWNHOLE ACOUSTIC SOURCE LOCALIZATION

(71) Applicant: Halliburton Energy Services, Inc., Houston, TX (US)

(72) Inventors: Yinghui Lu, The Woodlands, TX (US); Chung Chang, Houston, TX (US); Mark V. Collins, Spring, TX (US); Srinivasan Jagannathan, Houston, TX (US); Yibing Zheng, Houston, TX (US); Avinash Vinayak Taware, San Jose, CA (US)

(73) Assignee: Halliburton Energy Services, Inc., Houston, TX (US)

( * ) Notice: Subject to any disclaimer, the term of this patent is extended or adjusted under 35 U.S.C. 154(b) by 256 days.

(21) Appl. No.: 15/748,364

(22) PCT Filed: Sep. 7, 2016

(86) PCT No.: PCT/US2016/050551
§ 371 (c)(1),
(2) Date: Jan. 29, 2018

(87) PCT Pub. No.: WO2017/048565
PCT Pub. Date: Mar. 23, 2017

(65) Prior Publication Data
US 2018/0217021 A1    Aug. 2, 2018

Related U.S. Application Data

(60) Provisional application No. 62/220,723, filed on Sep. 18, 2015.

(51) Int. Cl.
*G01N 29/04* (2006.01)
*G01N 29/34* (2006.01)
(Continued)

(52) U.S. Cl.
CPC ........... *G01M 3/246* (2013.01); *E21B 47/101* (2013.01); *G01M 3/243* (2013.01); *G01N 29/036* (2013.01);
(Continued)

(58) Field of Classification Search
CPC ...... G01V 1/46; G01V 1/50; G01V 2210/588; G01V 1/52; G01V 1/006; G01V 1/44;
(Continued)

(56) References Cited

U.S. PATENT DOCUMENTS

| 4,888,740 A * | 12/1989 | Brie | G01V 1/50 367/30 |
| 2014/0056111 A1* | 2/2014 | Vu | E21B 47/0005 367/180 |
| 2016/0258281 A1* | 9/2016 | Mandal | E21B 47/09 |

OTHER PUBLICATIONS

International Application Serial No. PCT/US2016/050551, Search Report, dated Dec. 8, 2016, 3 pages.
(Continued)

*Primary Examiner* — Brandi N Hopkins
(74) *Attorney, Agent, or Firm* — Gilliam IP PLLC

(57) ABSTRACT

A method for operation of an acoustic tool, having a plurality of acoustic sensors, may include receiving acoustic waves from an acoustic source located at a depth in a borehole. A selected location (e.g., central location) of the acoustic sensor array may be positioned substantially at the depth of the acoustic source based on a symmetricity of an upper and lower section of a frequency-wavenumber (f-k) transform pattern with respect to a selected wavenumber. A radial distance from the acoustic source to the acoustic tool may be determined based on a theoretical f-k transform pattern used as a mask to filter measured data in the f-k domain.

20 Claims, 11 Drawing Sheets

(51) Int. Cl.

| | |
|---|---|
| *G01M 3/24* | (2006.01) |
| *G01N 29/42* | (2006.01) |
| *G01N 29/46* | (2006.01) |
| *G01N 29/036* | (2006.01) |
| *G01N 29/44* | (2006.01) |
| *G01N 29/14* | (2006.01) |
| *E21B 47/10* | (2012.01) |
| *G01N 29/22* | (2006.01) |

(52) U.S. Cl.
CPC ........... *G01N 29/14* (2013.01); *G01N 29/223* (2013.01); *G01N 29/42* (2013.01); *G01N 29/4472* (2013.01); *G01N 29/46* (2013.01); *G01N 2291/106* (2013.01)

(58) Field of Classification Search
CPC ....... G01V 2210/127; G01V 2210/125; G01V 1/40; G10K 15/02; E21B 47/10; E21B 47/09; E21B 47/101; E21B 47/0005
See application file for complete search history.

(56) References Cited

OTHER PUBLICATIONS

International Application Serial No. PCT/US2016/050551, Written Opinion, dated Dec. 8, 2016, 5 pages.

\* cited by examiner

US 10,598,563 B2

DOWNHOLE ACOUSTIC SOURCE LOCALIZATION

PRIORITY APPLICATION

This application claims benefit of U.S. Provisional Application Ser. No. 62/220,723 filed on 18 Sep. 2015, which application is incorporated by reference herein in its entirety.

BACKGROUND

Natural resources such as gas, oil, and water residing in a geological formation may be recovered by drilling a wellbore into the formation. A string of pipe (e.g., casing) is run into the wellbore in order to provide structural support for the wellbore sides. It is desirable to monitor the condition of the casing in the downhole environment. For example, it may be desirable to detect and locate leaks in the casing, tubing, or formation.

DETAILED DESCRIPTION

Some of the challenges noted above, as well as others, can be addressed by implementing the methods, apparatus, and systems described herein. In many examples, an acoustic tool may be used in a downhole environment to locate fluid flows (e.g., fluid leak) using the symmetricity of received acoustic waves in the f-k domain in order to axially locate an approximate center of the acoustic tool with relation to the leak. A radial distance from the leak to the acoustic tool may be determined using a theoretical f-k transform pattern as a mask to filter measured data in the f-k domain.

While subsequent figures and descriptions refer to the leak as being in a pipe wall, embodiments of the acoustic source localization methods are not limited to such a scenario. For example, the flow of a fluid from a formation crack in a downhole environment may also be located using the disclosed embodiments.

Figure 1:
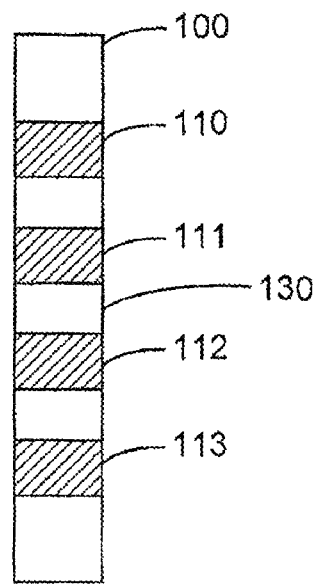
FIG. 1 is a block diagram showing an acoustic tool, according to various examples of the disclosure.

FIG. 1 is a block diagram showing an acoustic tool 100, according to various examples of the disclosure. The tool of FIG. 1 is for purposes of illustration only as other acoustic tools may be used with the subsequently described methods to achieve substantially similar results.

The tool 100 includes a plurality of acoustic sensors (e.g., hydro-phones) 110-113 that have the ability to receive audio signals (e.g., waves, data) from an acoustic source (e.g., fluid leak). Each sensor 110-113 is able to independently received an acoustic wave or data and transmit the resulting signal to a control circuit (see FIGS. 12-14). The control circuitry may be located downhole and/or on the surface. Processing of the signal, as described herein, may be accomplished downhole, on the surface, or portions of the processing split between downhole and the surface.

Figure 11:
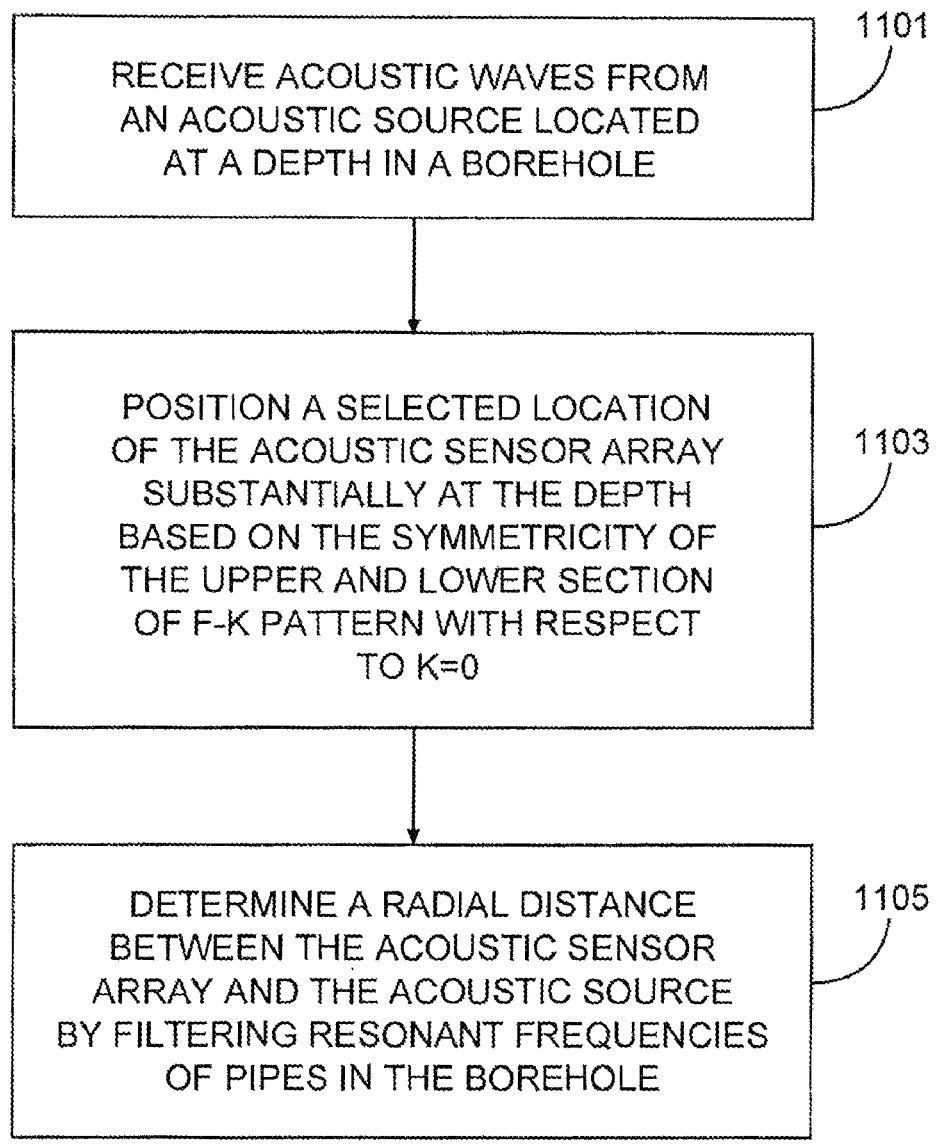
FIG. 11 is a flowchart showing a method for downhole acoustic source localization, according to various examples of the disclosure.
Figure 12:
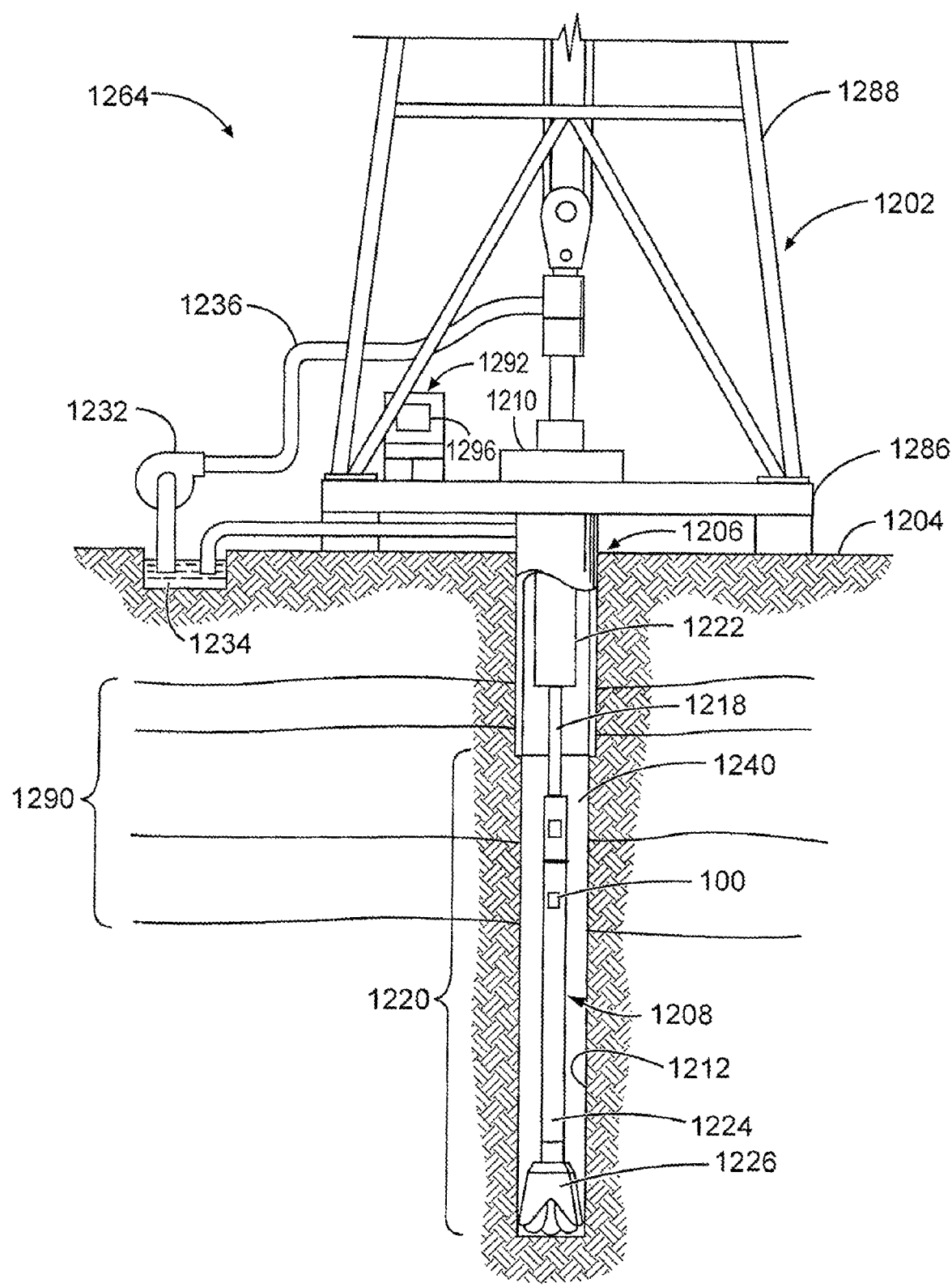
FIG. 12 is a diagram showing a drilling system, according to various examples of the disclosure.

The acoustic tool 100 may be located in a drill string tool housing to be used during a logging while drilling (LWD)/measurement while drilling (MWD) operation (see FIG. 11) or a wireline tool housing to be used during a wireline logging operation (see FIG. 12). Thus, the method used for transmitting the signals representing the received acoustic wave or data may vary depending on the environment. For example, the wireline embodiment may use a cable to transmit the signals to the surface while the drilling embodiment may use some form of telemetry (e.g., mud pulse telemetry) to transmit the signals to the surface.

The acoustic tool 100 is shown with a linear array of acoustic sensors 110-113. Other embodiments may use other forms of acoustic sensor arrays 110-113 that are not arranged in a linear orientation.

An approximate center location 130 of the acoustic tool 100 is shown and may be defined as a location on the tool 100 where a substantially equal number of sensors 110-113 are above the center location 130 as are below the center location 130. This center location 130 is used subsequently in the execution of an example of the method for downhole acoustic source localization.

Figure 2:
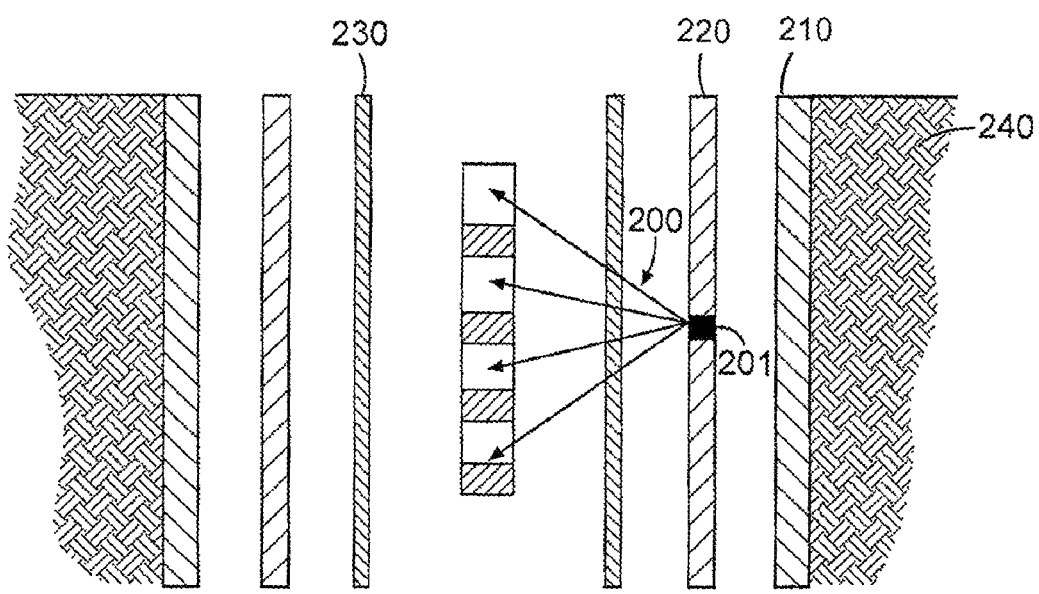
FIG. 2 is a cross-sectional diagram of a cased borehole in a geological formation including the acoustic tool, according to various examples of the disclosure.

FIG. 2 is a cross-sectional diagram of a cased borehole in a geological formation including the acoustic tool 100, according to various examples of the disclosure. The acoustic tool 100 is shown as a linear tool in a wireline embodiment. However, the disclosed examples are not limited to either of these examples.

A geological formation 240 has been drilled and cased with a pipe 220 (i.e., casing). The gap between the formation edge 210 and the casing 220 may be filled with concrete and/or a fluid. The acoustic tool 100 may be located within another concentric pipe 230 within the pipe 220.

A fluid (e.g., liquid, gas) leak 201 (i.e., acoustic source) is shown in the pipe 220. The fluid leak 201 may result in acoustic waves 200 being emitted by the leak 201. The fluid leak 201 in the pipe 220 is shown only for purposes of illustration as any fluid flow source that generates acoustic waves 200 (i.e., acoustic wave source) may be used by an example of the method for downhole acoustic source localization.

In water, an acoustic wavelength is multiple inches or longer for frequencies of 30 kHz or less. In contrast, a wall thickness of a casing may be measured in approximately fractional inches. Since the acoustic wavelength is considerably larger than the wall thickness of the pipe 230, acoustic waves can propagate through the walls of pipe 230, even at incident angles larger than the critical angle. In other words, it can be assumed that the wall of the pipe 230 between the acoustic source 201 and the sensor array 110-113 introduces relatively little acoustic interference to the wave propagation. Thus, beamforming methods may be used to localize the source directly.

On the other hand, since the acoustic wavelength is at the same order of the pipe diameter, the acoustic wave field will excite natural frequencies of the pipe 230 and, thus, generate resonant waves inside the pipe 230. Such resonant waves should be filtered out for acoustic source 201 localization.

In performing the method for acoustic source localization, a pattern for a theoretical f-k transform is determined and used as a mask to filter the measured data in the f-k domain. In determining the theoretical results of a point acoustic source in free space, the array waveforms of a single acoustic source, propagating in free space and received by the sensor array, are analyzed.

For example, a theoretical sensor array is used and assumed to include thousands of acoustic sensors with a sensor spacing of fractional inches in order to simulate an infinitely long sensor. The acoustic point source is assumed to be located at the center location of sensor array. The theoretical f-k transform pattern of the received acoustic waveforms at the sensor array is illustrated in FIG. 3.

Figure 3:
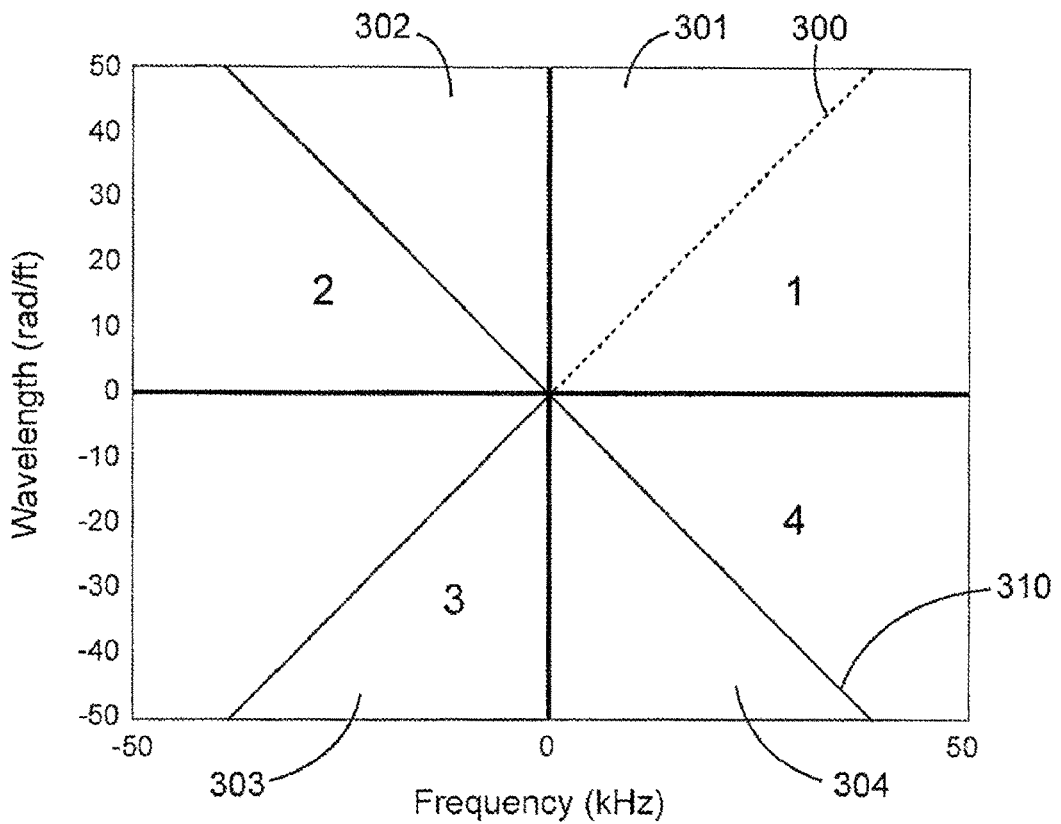
FIG. 3 is a plot showing a theoretical frequency-wavenumber (f-k) transform pattern of received acoustic signals assuming zero radial distance between source and sensor array, according to various examples of the disclosure.

FIG. 3 is a plot showing theoretical frequency-wavenumber (f-k) transform pattern of received acoustic signals assuming zero radial distance between source and sensor array, according to various examples of the disclosure. The f-k transform plot comprises frequency (in kilohertz (kHz)) along the x-axis and the wavenumber (in radians per foot (rad/ft)) along the y-axis. The wavenumber may be defined as the frequency of the waveform times the slowness of the waves across the acoustic sensor array.

The resulting plot includes four quadrants 301-304 that may be referred to as quadrants 1-4 and are formed by the 0 kHz y-axis and the 0 rad/ft x-axis. In this theoretical example, the radial distance between the theoretical acoustic sensor array and the acoustic source is assumed to be zero. The sensor array is also assumed to be theoretically infinite in length.

The spherical wave field generated by the acoustic source is received by the acoustic sensor array as two plane waves propagating up and down along the array axis (incident angle=90°). The f-k transforms of these up and down waves are illustrated in FIG. 3 as lines 300, 310 where the slope of the line 300 in the f-k domain is the wave speed in water (i.e., 206 μs/ft) which may be referred to as the reference speed of the wave in water (i.e., no pipes to cause interference). For example, the first line 300 may be the f-k transform of the waves below the central location of the acoustic source and the second line 310 may be the f-k transform of the waves above the central location of the acoustic source. The reference line 300 will be used in subsequent plots as a comparison of the wave speed in water without interference by any pipes.

Figure 4:
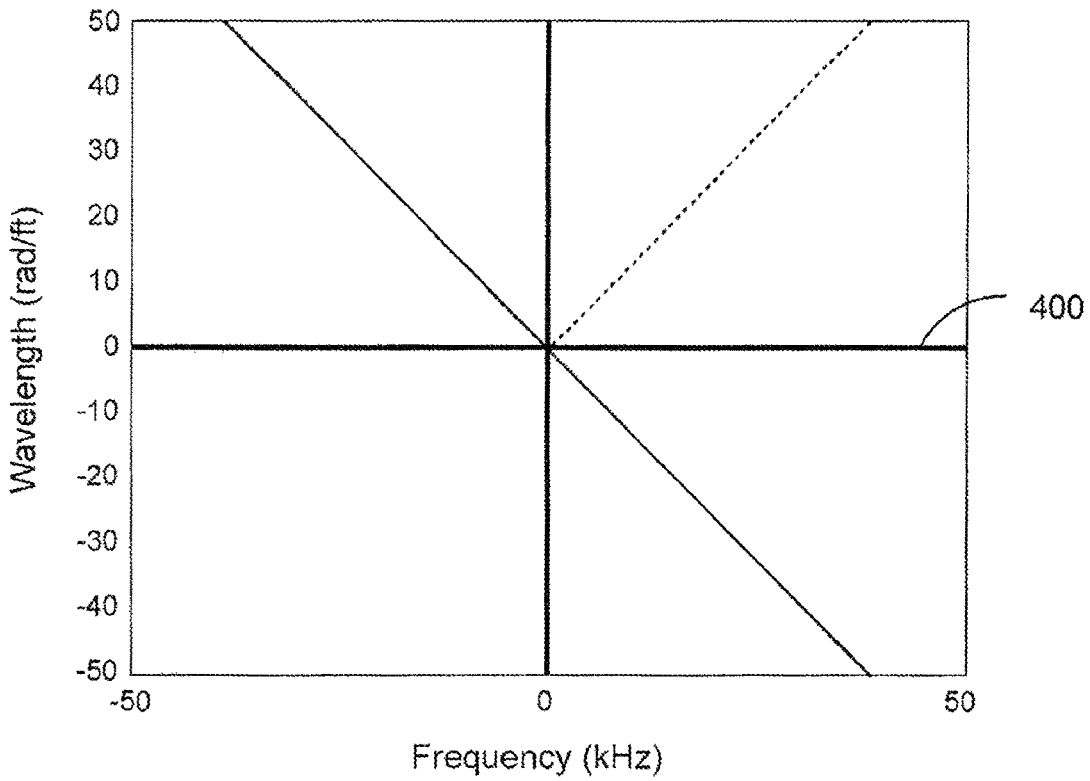
FIG. 4 is a plot showing another theoretical f-k transform pattern of received acoustic signals assuming an infinite radial distance between source and sensor array, according to various examples of the disclosure.

FIG. 4 is a plot showing another theoretical f-k transform pattern of received acoustic signals assuming an infinite radial distance between source and sensor array, according to various examples of the disclosure. The f-k transform plot comprises frequency (in kHz) along the x-axis and the wavenumber (in rad/ft) along the y-axis. The sensor array is still assumed to be theoretically infinite in length.

The example of FIGS. 3 and 4 assumes that the sensor array is still relatively centered on the acoustic source but the radial distance is now infinite. In this example, the spherical wave field generated by the acoustic source is received by the sensor array as a plane wave propagating from the broad side (incident angle=0). Therefore, the wavenumber values are essentially zero as represented by the f-k transform line 400 along the zero wavenumber axis having a slope of zero. This is an indication of an infinite apparent wave speed along the sensor array axis.

Figure 5:
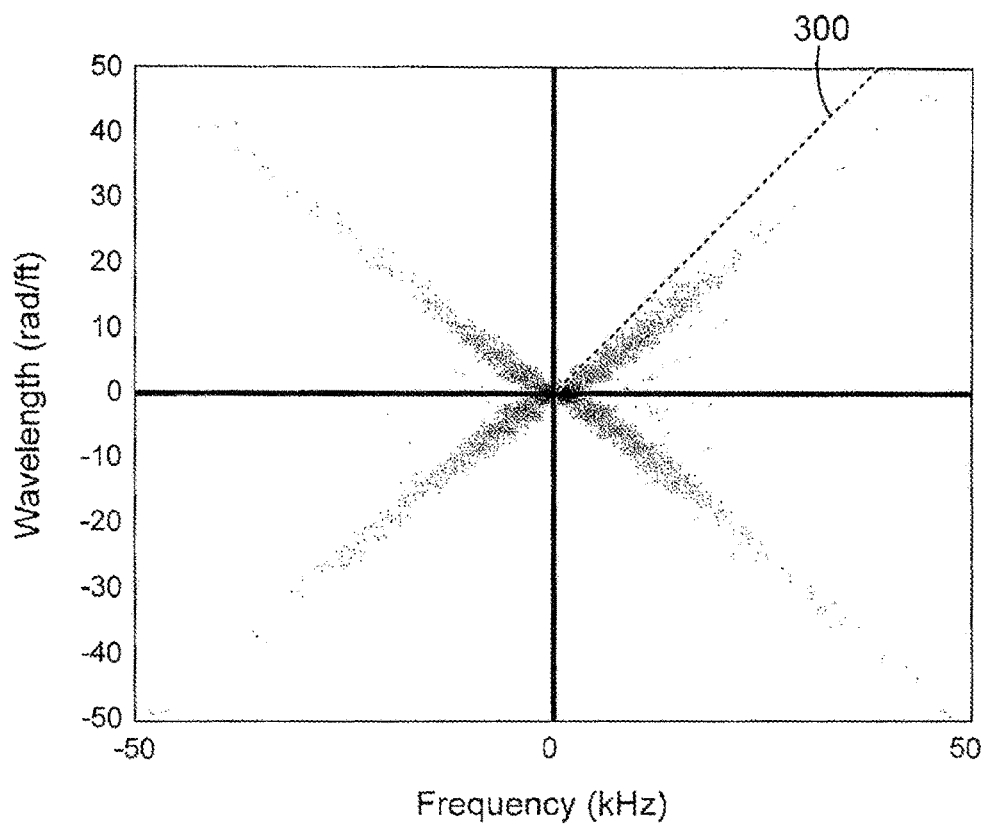
FIG. 5 is a plot showing another theoretical f-k transform pattern of received acoustic signals assuming an intermediate radial distance between source and sensor array, according to various examples of the disclosure.

FIG. 5 is a plot showing another theoretical f-k transform pattern of received acoustic signals assuming an intermediate radial distance between source and sensor array, according to various examples of the disclosure. The f-k transform plot comprises frequency (in kHz) along the x-axis and the wavenumber (in rad/ft) along the y-axis. The sensor array is still assumed to be relatively centered on the acoustic source but the radial distance is now some intermediate radial distance between zero and infinity and the sensor array is now assumed to be some finite length.

This figure illustrates that the spherical wave field generated by the acoustic source is received by the sensor array as two predominant plane waves propagating towards the two ends of the array. The incident angles of these two plane waves is less than 90°, as represented by the reference line 300, and greater than 0°.

Figure 6:
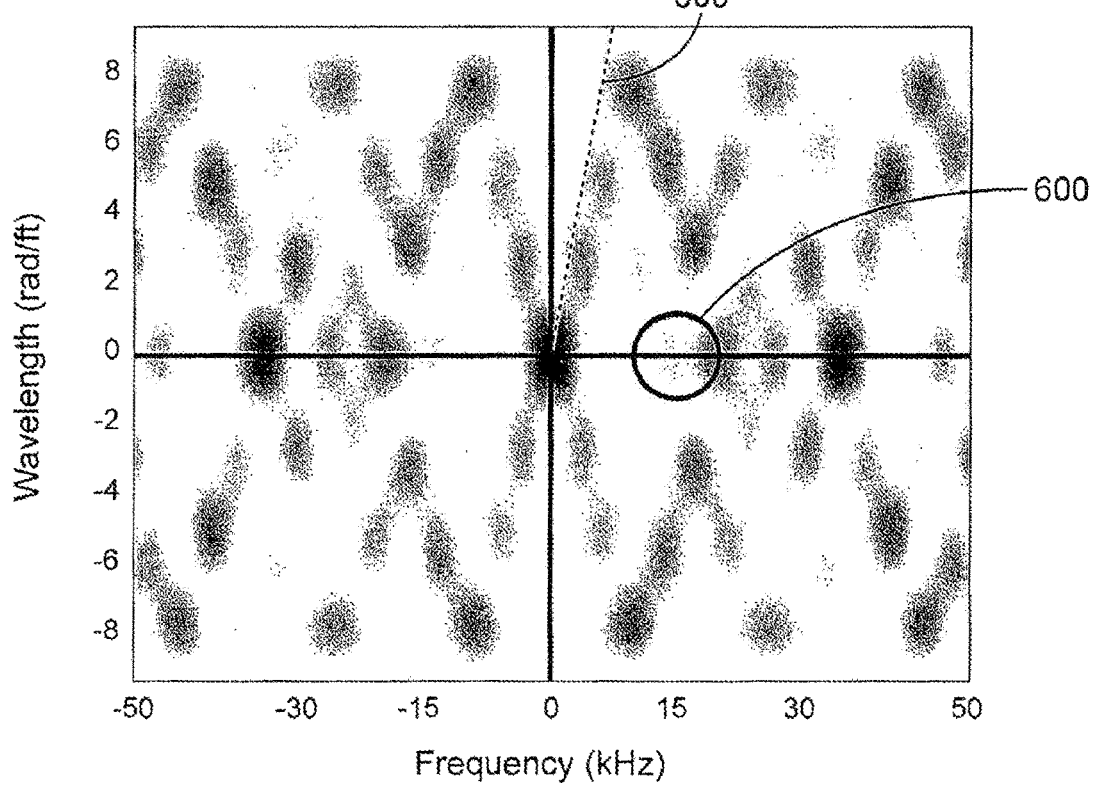
FIG. 6 is a plot showing another theoretical f-k transform pattern of received acoustic signals assuming an intermediate radial distance between source and sensor array, according to various examples of the disclosure.

FIG. 6 is a plot showing another theoretical f-k transform pattern of received acoustic signals assuming an intermediate radial distance between source and sensor array, according to various examples of the disclosure. The sensors of the sensor arrays of the previous examples (i.e., FIGS. 3-5) are assumed to have the sensors spaced relatively close such that the sensors theoretically have no gap between adjacent sensors. Adjacent sensors of the example plot of FIG. 6 are now spaced a more practical distance apart (e.g., measured in inches).

In the plot of FIG. 6, the pattern of the f-k transform essentially remains the same as in the plot of FIG. 5, showing two predominant plane waves propagating towards the two ends of the sensor array. The difference between the examples of FIG. 5 and FIG. 6 is the spatial and temporal aliasing introduced by the larger sensor spacing. In this example, the alias-free wavenumber range is reduced to approximately 9.5 rad/ft. At an incident angle=90°, the corresponding alias-free temporal frequency is approximately 7.5 kHz as represented by the end of the reference line 300. At an incident angle=0°, a typical corresponding alias-free temporal frequency is illustrated by the circle at k=0 where k may be defined as a wavenumber and k=0 represents a plane wave propagating substantially perpendicular to the sensor array. This limit frequency depends on the receiver spacing.

Figure 7:
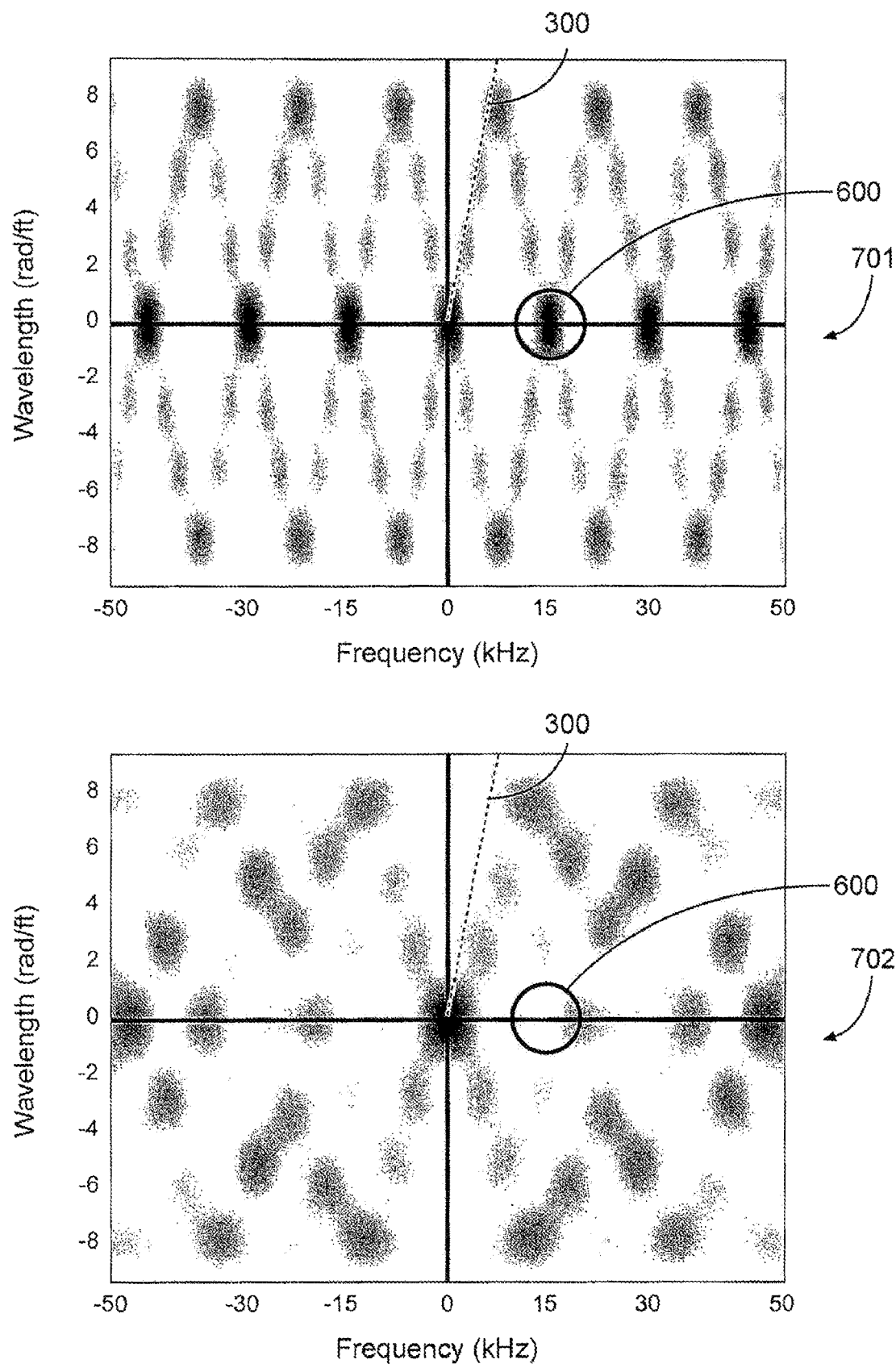
FIG. 7 are plots showing theoretical f-k transform patterns of received acoustic signals assuming varying radial distances between source and sensor array, according to various examples of the disclosure.

FIG. 7 illustrates plots showing theoretical f-k transform patterns of received acoustic signals assuming varying radial distances between source and sensor array, according to various examples of the disclosure. The top plot 701 shows the f-k transform patterns of received acoustic signals when the sensor array is relatively close to the source as compared to the bottom plot 702. The bottom plot 702 shows the f-k transform patterns of the received acoustic signals when the sensor array is relatively distant from the source as compared to the top plot 701. Comparing the slope of each signal to the reference line 300 in each plot, it can be seen that as the sensor array is moved further from the acoustic source, the slope of the dominant plane waves decreases. Each plot is highlighted at the circle 600 to show the received signal at alias-free limit frequency at the varying distances.

As described previously, the examples of FIGS. 3-7 assume that the sensor array is centered on the acoustic source. The example plots of FIGS. 8 and 9 assume that the sensor array is either above or below the acoustic source in addition to different adjacent sensor spacing distances.

Figure 8:
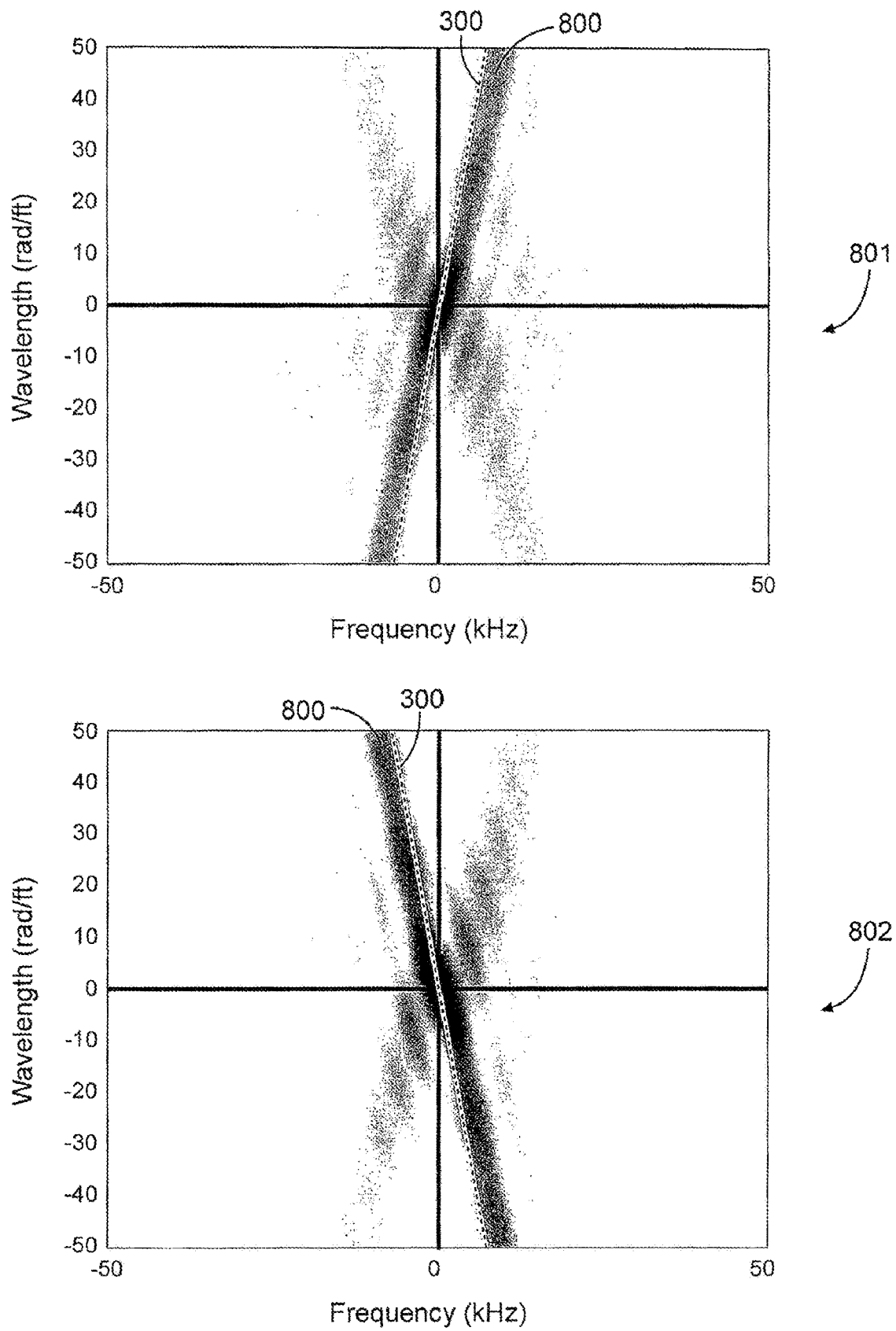
FIG. 8 illustrates plots showing theoretical f-k transform patterns of received acoustic signals assuming a fixed source-to-sensor array radial distance with the source asymmetrically positioned relative to the array and adjacent sensors spaced relatively close, according to various examples of the disclosure.

FIG. 8 illustrates plots 801, 802 showing theoretical f-k transform patterns of received acoustic signals assuming a fixed source-to-sensor array radial distance with the source asymmetrically positioned relative to the array and adjacent sensors spaced relatively close, according to various examples of the disclosure. The relatively close adjacent sensor distances are closer relative to the adjacent sensor spacing of the example of FIG. 9. For example, the adjacent sensor spacing for the example of FIG. 8 may be measured in fractional inches while the adjacent sensor spacing of the example of FIG. 9 may be measured in inches.

The top plot 801, in one example, shows theoretical f-k transform patterns of received signals when the center location of the sensor array is moved down so that the quantity of sensors above the acoustic source is less than the quantity of sensors below the acoustic source. The bottom plot 802 then shows the theoretical f-k transform patterns of the received signals when the center location of the sensor array is moved up so that the quantity of sensors above the acoustic source is greater than the quantity of sensors below the acoustic source. In other words, the sensor array is asymmetrically positioned axially with respect to the source.

In another example, the top plot 801 may show the theoretical f-k transform patterns of received signals when the center location of the sensor array is moved up so that the array receives waves propagating from the acoustic source below the array (vertically with respect to the center of the array). In such an example, the bottom plot 802 then shows the theoretical f-k transform patterns of the received signals when the center location of the sensor array is moved down so that the array receives waves propagating from the acoustic source above the array (vertically with respect to the center of the array).

These plots 801, 802 show the f-k transform lines relative to the reference line 300. Reference line 300 represents the cases where the radial distance is 0 and the acoustic source is right below or above the tool. When the radial distance is not zero, line 800 is observed.

Figure 9:
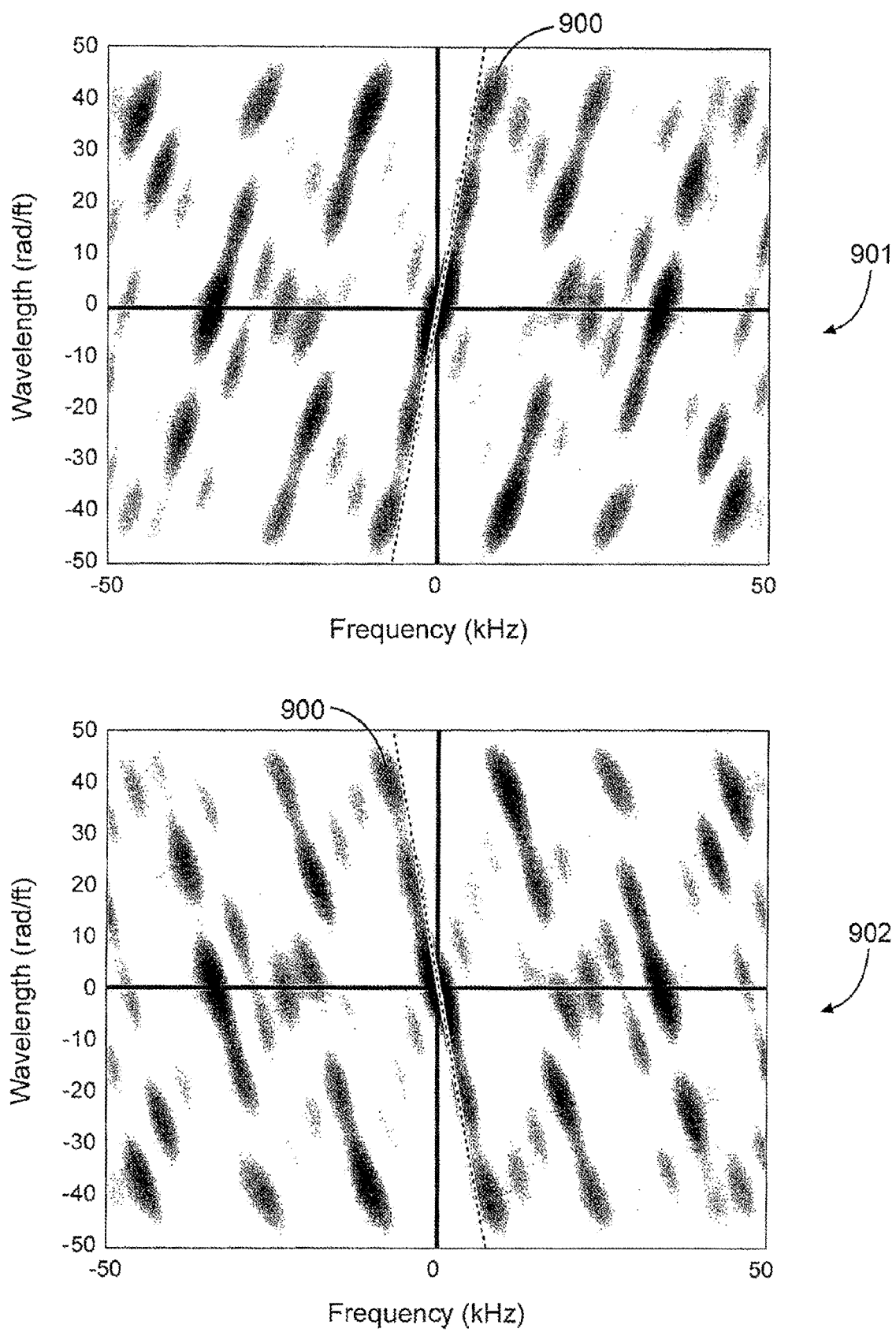
FIG. 9 illustrates plots showing theoretical f-k transform patterns of received acoustic signals assuming a fixed source-to-sensor array radial distance with the source asymmetrically positioned relative to the array and adjacent sensors spaced relatively distant, according to various examples of the disclosure.

FIG. 9 illustrates plots 901, 902 showing theoretical f-k transform patterns of received acoustic signals assuming a fixed source-to-sensor array radial distance with the source asymmetrically positioned relative to the array and adjacent sensors spaced relatively distant, according to various examples of the disclosure.

With the relatively large adjacent sensor spacing, there is aliasing in the f-k domain but the predominant line 900 is still observable and more importantly the aliasing follows the same pattern of the predominant line 900.

The top plot 901, in one example, shows theoretical f-k transform patterns of received signals when the center location of the sensor array is moved down so that the quantity of sensors above the acoustic source is less than the quantity of sensors below the acoustic source. The bottom plot 902 then shows the theoretical f-k transform patterns of the received signals when the center location of the sensor array is moved up so that the quantity of sensors above the acoustic source is greater than the quantity of sensors below the acoustic source. In other words, the sensor array is asymmetrically positioned axially with respect to the source.

Figure 10:
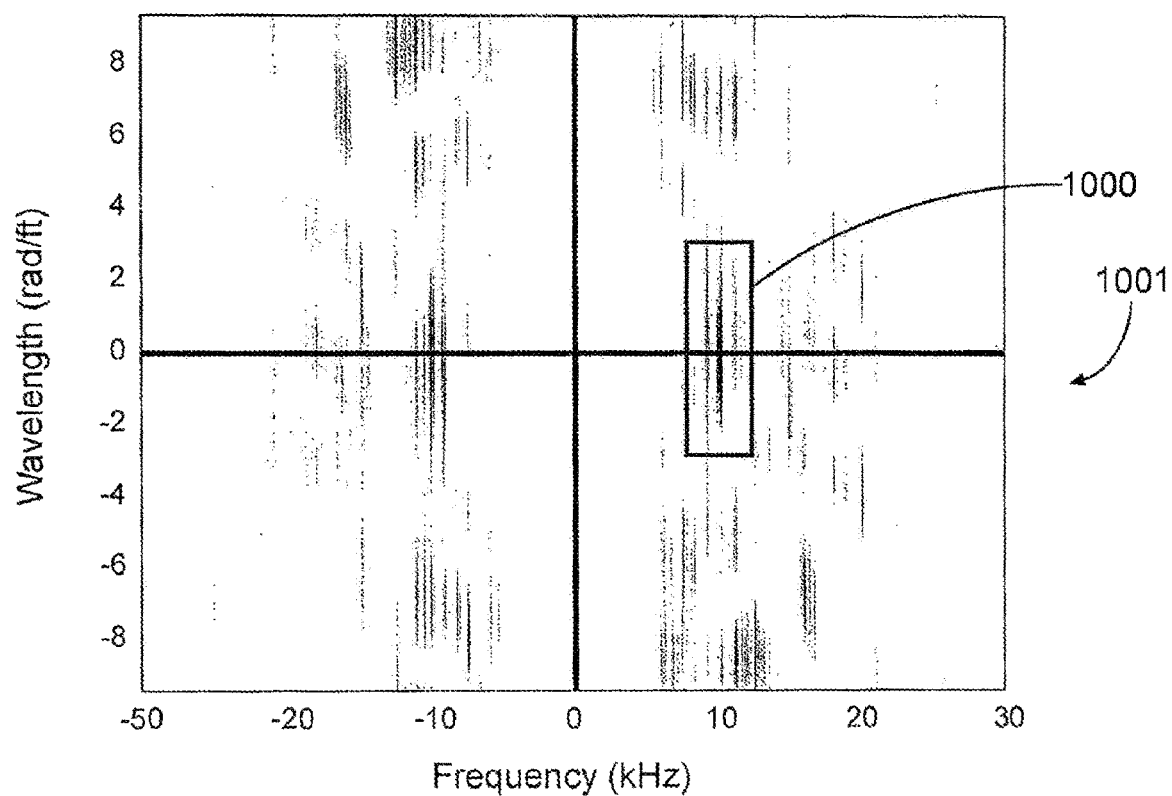
FIG. 10 illustrates a plot showing an f-k transform pattern for a measured set of data and a plot for a theoretical f-k transform pattern, according to various examples of the disclosure.
Figure 10:
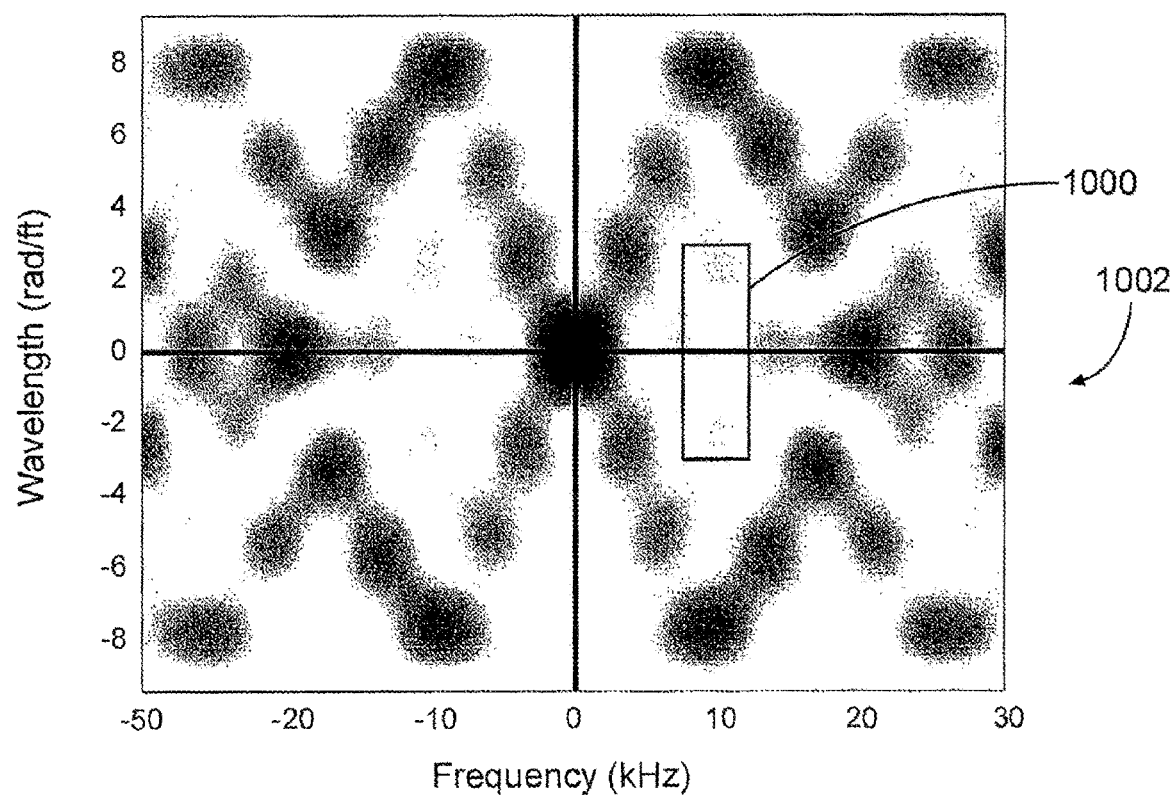

FIG. 10 illustrates a plot 1001 showing an f-k transform pattern for a measured set of data and a plot 1002 for a theoretical f-k transform pattern, according to various examples of the disclosure. Since the f-k transform pattern of an acoustic source in free space (e.g., water with no pipes) is known, as described previously, the theoretical f-k transform pattern 1002 can be compared with that of the experimental data 1001 to identity signatures.

For example, the top plot 1001 shows a bright stripe around 10 kHz in the data f-k pattern that does not show up in the bottom plot 1002 of the theoretical pattern. This stripe, illustrated by the box 1000, identifies the resonant frequencies from the acoustic waves interacting with the casing, based on the estimated radial resonant frequencies of the casing.

In one example, the radial resonant frequencies of a casing may be estimated for relatively thin walled pipes (e.g., thickness <10% of diameter of pipe) by:

$$f = \frac{1}{2\pi} \times \sqrt{4E/D^2 \delta}$$

where f is the radial resonant frequency in Hz, E is Young's modulus $2 \times 10^{11}$ (Newtons/meter$^2$), $\delta$ is the density constant 7850 Kg/m$^3$, and D is the pipe diameter in meters.

The theoretical f-k transform pattern developed previously may now be used as a mask to remove the interference of the pipe. For example, the mask may be multiplied with the measured data so that the f-k pattern with no signal at the location indicated by the box (1000 of plot 1002) removes the interference at the same location (1000 of plot 1001) in the measured data plot 1001.

FIG. 11 is a flowchart showing a method for downhole acoustic source localization, according to various examples of the disclosure. This method may be used to both axially and radially locate an acoustic source (e.g., fluid flow, leak) in the borehole using the acoustic sensor array of the sensor tool. As discussed previously, the sensor array comprises a plurality of sensors (e.g., hydrophones, linear array). By checking the symmetricity of the upper and lower sections of the f-k pattern (with respect to k=0), the propagation direction of the received wave can be determined and, thus, the up/down direction of the acoustic source relative to the sensor array can be determined.

In block 1101, acoustic waves are received by the acoustic sensor array at a depth in a borehole. In block 1103, a controller (as described subsequently) axially positions a selected location of the acoustic sensor array substantially at the depth based on a symmetricity, with respect to a selected wavenumber, of an upper and lower section of an f-k transform pattern of the received acoustic waves. In an example, the pattern of the f-k transform of the received acoustic waves is symmetrical with respect to the selected wavenumber. The selected location may be substantially at a center location of the acoustic sensor array such that the plurality of acoustic sensors are divided into two equal groups of sensors by the selected location.

The controller may determine when a pattern of the f-k transform of the received acoustic waves is symmetrical with respect to the selected wavenumber (e.g., wavenumber 0). The symmetricity of the f-k transform pattern may be determined by a comparison of received total energy from each of first and second groups of acoustic sensors of the plurality of acoustic sensors. This may determine a total energy from each of the first and second groups of acoustic sensors in response to performing a Discrete Fourier Transform on the acoustic waves received by each of the first and second groups of acoustic sensors.

In block 1105, a radial distance between the sensor array and the acoustic source is determined by filtering, from the received acoustic waves, resonant frequencies of a pipe. The filtering may include filtering the received acoustic waves in the f-k domain to generate filtered f-k data. The radial distance may then be determined in response to a largest total energy, of a plurality of total energies, associated with the radial distance, wherein each of the plurality of total energies is associated with a different radial distance and is determined from the filtered f-k data.

The filtering of the acoustic waves in the f-k domain to generate the filtered f-k data may include converting the filtered f-k data for each of a plurality of radial distances to filtered time-spatial domain data for each of the plurality of radial distances. The radial distance between the acoustic sensor array and the acoustic source may then be determined by applying beamforming to the plurality of filtered time-spatial domain data.

The beamforming (i.e., spatial filtering) may be performed in multiple different ways. For example, the beamforming may be by conventional beamforming, Multiple Signal Classification (MUSIC), Capon's beam-forming, or various parametric methods. These methods are for purposes of illustration only as other methods for array signal processing may also be used. By way of example only, both conventional beamforming and Capon's beamforming are described subsequently.

The described beamforming methods fuse various simultaneously acquired sensor signals to localize the acoustic source. To illustrate the principle underlying spatial filtering methods, consider a narrowband, far-field acoustic source s(t). If acoustic waves emitted from that source impinge a linear array at an angle $\theta$ with respect to the normal to the array, the sensors within the array measure signals (expressed as a vector X(t)):

$$X(t) = a(\theta) s(t) + n(t),$$

where $a(\theta)$ is a complex-valued vector expressing the amplitude attenuation and phase shift undergone by the signal on its path from the source to the respective sensors, and n(t) is a vector expressing the contribution of noise. Conversely, an unknown source signal can be estimated by fusing the measured signals, in accordance with:

$$y(t) = \frac{1}{L}\sum_{i=1}^{L} a_i(\theta) \cdot x_i(t) = \frac{a^H(\theta)}{L} X(t),$$

where L is the number of sensors and the superscript H denotes the conjugate transpose (i.e., the Hermitian). The vector $a(\theta)$ encapsulates the forward model of phase propagation, and is often referred to as the steering vector. In the simple case of a uniform medium in which the waves travel at a constant speed of sound c, with a wave vector $k=\omega/c$, $a(\theta)$ takes the form:

$$a(\theta) = [1 \; e^{-ikd \cos \theta} \ldots e^{-i(L-1)kd \cos \theta}]^T,$$

where d is the distance between adjacent sensors of a uniform array.

More generally, array signal processing involves expressing the fused signal y(t) as a weighted linear combination of the measured signals, $$y(t) = \sum_{i=1}^{L} w^*_i(t) = w^H X(t),$$

and determining the complex-valued weight vector w based on a suitable heuristic.

In conventional beamforming, the weights are selected to maximize the output power of the fused signal at a given incident angle $\theta$:

$$P(w) = \frac{1}{N}\sum_{i=1}^{N} |y(t)|^2 = \frac{1}{N}\sum_{i=1}^{N} w^H X(t) X^H(t) w = w^H \hat{R} w,$$

where $\hat{R}$ is the sample covariance matrix $$\hat{R} = \frac{1}{N}\sum_{i=1}^{N} X(t) X^H(t).$$

The resulting optimization problem takes the form $$\max_w E\{w^H X(t) X^H(t) w\} = \max_w \{E[|s(t)|^2] \cdot |w^H a(\theta)|^2 + w^H C_n w\}$$

subject to the constraint, $|w|=1$. The non-trivial solution to this problem is:

$$w = \frac{a(\theta)}{a^H(\theta) a(\theta)} = \frac{a(\theta)}{L}.$$

In Capon's beamforming method, the optimization problem takes the form:

$$\min_w E\{w^H X(t) X^H(t) w\} = \min_w \{E[|s(t)|^2] \cdot |w^H a(\theta)|^2 + w^H C_n w\}$$

subject to the constraint $|w^H a(\theta)|=1$. This method fixes the gain at the incident angle $\theta$ and minimizes the noise contribution. The solution is:

$$w = \frac{\hat{R}^{-1} a(\theta)}{a^H(\theta) \hat{R}^{-1} a(\theta)}.$$

As can be seen, Capon's beamforming method incorporates the data (reflected in the sample covariance matrix $\hat{R}$) with the a-priori known forward model and is thus one example of so-called "adaptive" spatial filtering methods. Additional methods are known to those of ordinary skill in the art.

The above-described beamforming methods apply under the assumption that the source signal is far away from the sensor array (far-field assumption) such that the time delays of individual sensors are a function of the incident angle θ only. To process near-field signals and to include the effects of different media between the source and sensor array, the steering vector a(θ) is suitably modified, in accordance with various embodiments, to become a function a(θ, $r_{spherical}$) of θ where $r_{spherical}$ is the range of the source, i.e., the distance of the source from the sensor in spherical coordinates (which differs from the perpendicular radial distance of the source from the wellbore axis).

The modified steering vector a(θ, $r_{spherical}$) may depend on a configuration and condition of the wellbore and surrounding formation, taking into account, for example, the geometry and material properties of various layers and their effect on sound propagation (e.g., the resulting sound velocities in rock, mud, cement, etc.). Further, to process broadband signals, the measured signals are divided into narrow spectral bands and, following processing of the narrowband signals, the results are combined in manners well-known to those of ordinary skill in the art.

Accordingly, in various embodiments, the set of acoustic signals measured at the plurality of sensors is processed by "scanning" a two-dimensional region of interest (along depth and radial-distance) for possible source locations by computing, for each of a plurality of "putative" source locations (e.g., characterized by θ and $r_{polar}$, which can both be straightforwardly computed from the radial distance and the depth, relative to the sensor location), the fused signal y(t), using a suitable array-signal processing method (e.g., conventional beamforming or Capon's beamforming). The computed energy level reaches a maximum value in the vicinity of the actual acoustic source location. In the absence of a significant acoustic signal source, only low energy levels will be exhibited. In the case of multiple acoustic sources, high energy levels will be found at multiple locations. Accordingly, acoustic-signal detection and processing in accordance herewith may facilitate simultaneously detecting multiple fluid flows.

FIG. 12 is a diagram showing a drilling system 1264, according to various examples of the disclosure. The system 1264 includes a drilling rig 1202 located at the surface 1204 of a well 1206. The drilling rig 1202 may provide support for a drillstring 1208. The drillstring 1208 may operate to penetrate the rotary table 1210 for drilling the borehole 1212 through the subsurface formations 1290. The drillstring 1208 may include a drill pipe 1218 and a bottom hole assembly (BHA) 1220 (e.g., drill string), perhaps located at the lower portion of the drill pipe 1218.

The BHA 1220 may include drill collars 1222, a down hole tool 1224 including the acoustic tool 100, and a drill bit 1226. The drill bit 1226 may operate to create the borehole 1212 by penetrating the surface 1204 and the subsurface formations 104. The downhole tool 1224 may comprise any of a number of different types of tools besides the acoustic tool 100. The acoustic tool 100 may be used in MWD/LWD operations within a borehole 1212. Using the acoustic tool 100 during the MWD/LWD operations may provide leak data to the surface (e.g., hardwired, telemetry) on already boreholes being drilled or cased and cemented portions of the borehole 1212. The leak data may include leaks in the casing, fluid flows of the formation, or other acoustic sources.

During drilling operations within the cased borehole 1212, the drillstring 1208 (perhaps including the drill pipe 1218 and the BRA 1220) may be rotated by the rotary table 1210. Although not shown, in addition to or alternatively, the BHA 1220 may also be rotated by a motor (e.g., a mud motor) that is located down hole. The drill collars 1222 may be used to add weight to the drill bit 1226. The drill collars 1222 may also operate to stiffen the bottom hole assembly 1220, allowing the bottom hole assembly 1220 to transfer the added weight to the drill bit 1226, and in turn, to assist the drill bit 1226 in penetrating the surface 1204 and subsurface formations 1214.

During drilling operations within the cased borehole 1212, a mud pump 1232 may pump drilling fluid (sometimes known by those of ordinary skill in the art as "drilling mud") from a mud pit 1234 through a hose 1236 into the drill pipe 1218 and down to the drill bit 1226. The drilling fluid can flow out from the drill bit 1226 and be returned to the surface 1204 through an annular area 1240 between the drill pipe 1218 and the sides of the borehole 1212. The drilling fluid may then be returned to the mud pit 1234, where such fluid is filtered. In some examples, the drilling fluid can be used to cool the drill bit 1226, as well as to provide lubrication for the drill bit 1226 during drilling operations. Additionally, the drilling fluid may be used to remove subsurface formation cuttings created by operating the drill bit 1226.

A workstation 1292 including a controller 1296 may include modules comprising hardware circuitry, a processor, and/or memory circuits that may store software program modules and objects, and/or firmware, and combinations thereof that are configured to execute the method of FIG. 11. For example, the workstation 1292 with controller 1296 may be configured to locate an acoustic source (e.g., leak, fluid flow), according to the methods described previously.

Thus, in various examples, components of a system operable to locate an acoustic source, as described herein or in a similar manner, can be realized in combinations of hardware and/or processor executed software. These implementations can include a machine-readable storage device having machine-executable instructions, such as a computer-readable storage device having computer-executable instructions. Further, a computer-readable storage device may be a physical device that stores data represented by a physical structure within the device. Such a physical device is a non-transitory device. Examples of machine-readable storage devices can include, but are not limited to, read only memory (ROM), random access memory (RAM), a magnetic disk storage device, an optical storage device, a flash memory, and other electronic, magnetic, and/or optical memory devices.

Figure 13:
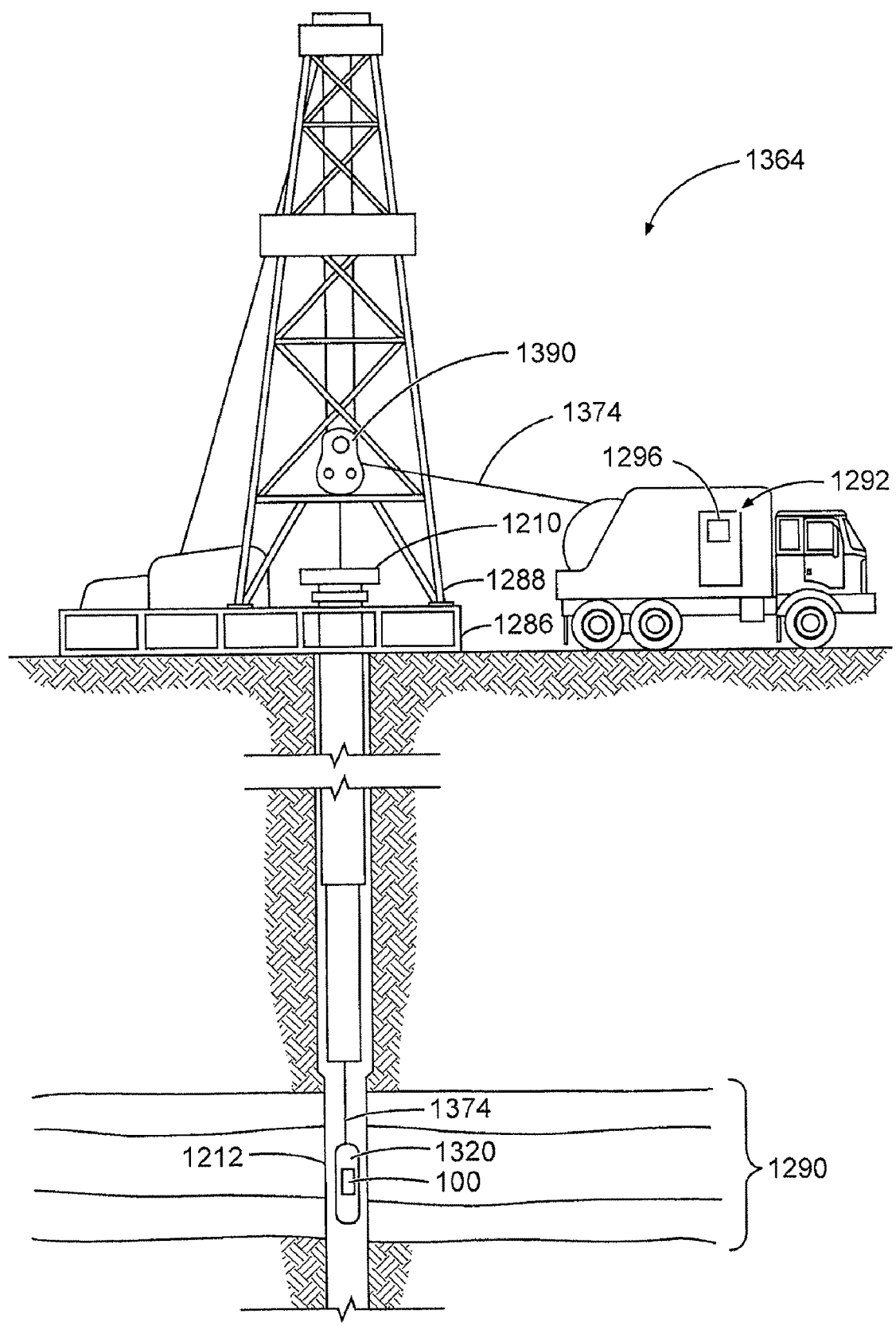
FIG. 13 is a diagram showing a wireline system, according to various examples of the disclosure.

FIG. 13 is a diagram showing a wireline system 1364, according to various examples of the disclosure. The system 1364 may comprise a wireline logging tool body 1320, as part of a wireline logging operation in a cased and cemented borehole 1212, that includes the acoustic tool 100 as described previously.

A drilling platform 1286 equipped with a derrick 1288 that supports a hoist 1390 can be seen. Drilling oil and gas wells is commonly carried out using a string of drill pipes connected together so as to form a &dishing that is lowered through a rotary table 1210 into the cased borehole 1212. Here it is assumed that the drillstring has been temporarily removed from the borehole 1212 to allow the wireline logging tool body 1320, such as a probe or sonde with the acoustic tool 100, to be lowered by wireline or logging cable 1374 (e.g., slickline cable) into the borehole 1212. Typically, the wireline logging tool body 1320 is lowered to the bottom of the region of interest and subsequently pulled upward at a substantially constant speed.

During the upward trip, at a series of depths, the acoustic tool may have the selected location between groups of sensors (e.g., central location) positioned at substantially the same depth as an acoustic source, as described previously. The wireline data (e.g., received wave data) may be communicated to a surface logging facility (e.g., workstation 1292) for processing, analysis, and/or storage. The logging facility 1292 may be provided with electronic equipment for various types of signal processing as described previously. The workstation 1292 may have a controller 1296 that is coupled to the acoustic tool 100 through the wireline 1374 or telemetry in order to receive wave data from the acoustic tool regarding the acoustic waves received from the acoustic source.

Figure 14:
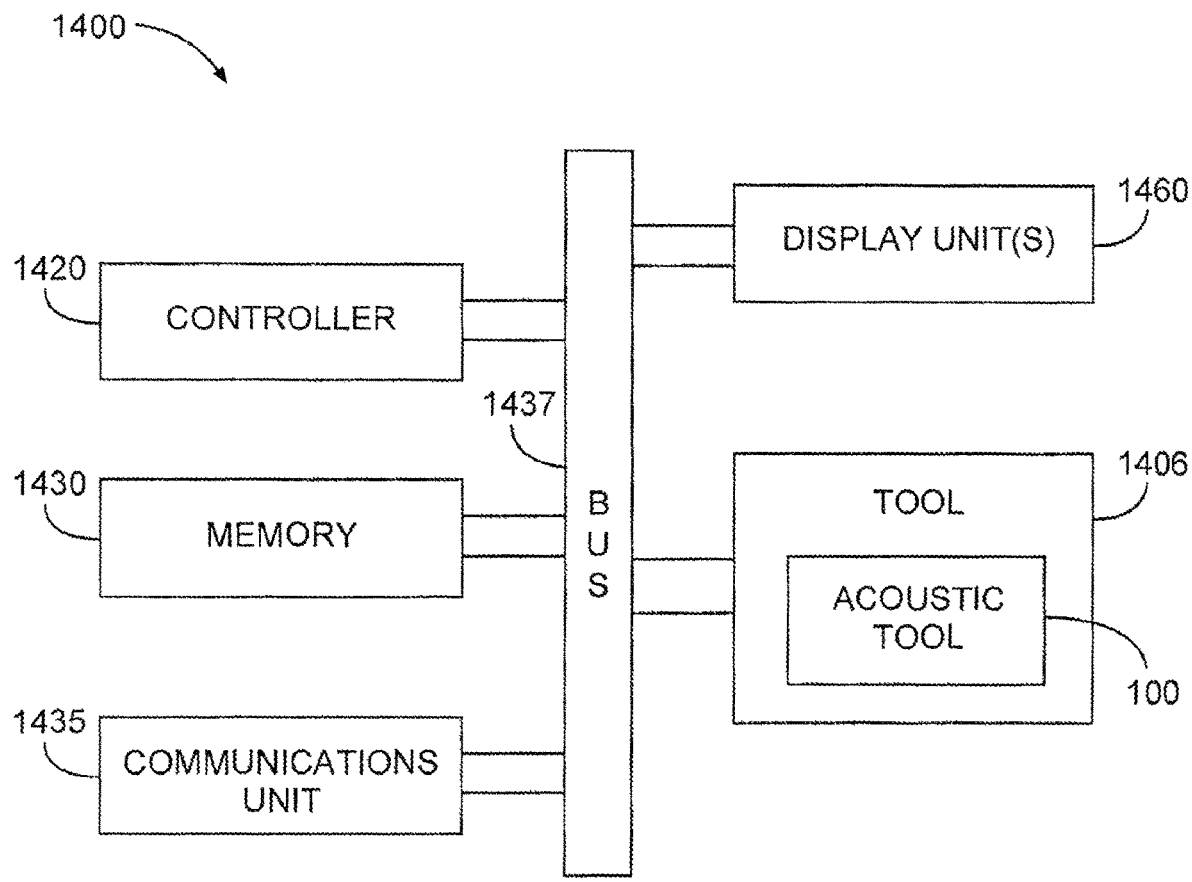
FIG. 14 is a block diagram of an example system operable to implement the activities of multiple methods, according to various examples of the disclosure.

FIG. 14 is a block diagram of an example system 1400 operable to implement the activities of disclosed methods, according to various examples of the disclosure. The system 1400 may include a tool housing 1406 having the acoustic tool 100 such as that illustrated in FIG. 1. The system 1400 may be configured to operate in accordance with the teachings herein to perform formation independent cement evaluation measurements in order to determine the quality of cement between the casing and the formation. The system 1400 of FIG. 14 may be implemented as shown in FIGS. 12 and 13 with reference to the workstation 1292 and controller 1296.

The system 1400 may include a controller 1420, a memory 1430, and a communications unit 1435. The memory 1430 may be structured to include a database. The controller 1420, the memory 1430, and the communications unit 1435 may be arranged to operate as a processing unit to control operation of the acoustic tool 100 and execute any methods disclosed herein. One or more controllers 1420 and/or memory 1430 may be included in the acoustic tool 100 for processing of signals on the tool 100 as well as other control functions of the tool 100.

The communications unit 1435 may include downhole communications for acoustic sensors in the wellbore. Such downhole communications can include a telemetry system. The communications unit 1435 may use combinations of wired communication technologies and wireless technologies at frequencies that do not interfere with on-going measurements.

The system 1400 may also include a bus 1437, where the bus 1437 provides electrical conductivity among the components of the system 1400. The bus 1437 can include an address bus, a data bus, and a control bus, each independently configured or in an integrated format. The bus 1437 may be realized using a number of different communication mediums that allows for the distribution of components of the system 1400. The bus 1437 may include a network. Use of the bus 1437 may be regulated by the controller 1420.

The system 1400 may include display unit(s) 1460 as a distributed component on the surface of a wellbore, which may be used with instructions stored in the memory 1430 to implement a user interface to monitor the operation of the acoustic tool 100 or components distributed within the system 1400. The user interface may be used to input parameter values for thresholds such that the system 1400 can operate autonomously substantially without user intervention in a variety of applications. The user interface may also provide for manual override and change of control of the system 1400 to a user. Such a user interface may be operated in conjunction with the communications unit 1435 and the bus 1437. Many examples may thus be realized. A few examples of such examples will now be described.

Example 1 is a method comprising: receiving, with an acoustic sensor array having a plurality of acoustic sensors, acoustic waves from an acoustic source located at a depth in a borehole; and axially positioning a selected location of the acoustic sensor array substantially at the depth based on a symmetricity, with respect to a selected wavenumber, of an upper and lower section of a frequency-wavenumber (f-k) transform pattern of the received acoustic waves.

In Example 2, the subject matter of Example 1 optionally includes wherein the selected location is substantially at a center location of the acoustic sensor array such that the plurality of acoustic sensors are divided into two equal groups of sensors by the selected location.

In Example 3, the subject matter of any one or more of Examples 1-2 optionally include wherein positioning the selected location of the acoustic sensor array comprises determining when the f-k transform pattern of the received acoustic waves is symmetrical with respect to the selected wave number.

In Example 4, the subject matter of Example 3 optionally includes wherein the selected wavenumber is zero.

In Example 5, the subject matter of any one or more of Examples 1-4 optionally include wherein positioning the selected location of the acoustic sensor array comprises determining a received total energy from each of the plurality of acoustic sensors in response to performing a Discrete Fourier Transform on the acoustic waves received by each of the plurality of acoustic sensors.

In Example 6, the subject matter of any one or more of Examples 1-5 optionally include determining a radial distance between the acoustic sensor array and the acoustic source.

In Example 7, the subject matter of Example 6 optionally includes wherein determining the radial distance comprises filtering, from the received acoustic waves, resonant frequencies of a pipe.

In Example 8, the subject matter of Example 7 optionally includes wherein filtering the resonant frequencies of the pipe from the received acoustic waves comprises filtering the received acoustic waves in an f-k domain to generate filtered f-k data, the method further comprising: determining the radial distance in response to a largest total energy, of a plurality of total energies, associated with the radial distance, wherein each of the plurality of total energies is associated with a different radial distance and is determined from the filtered f-k data.

In Example 9, the subject matter of any one or more of Examples 7-8 optionally include wherein filtering the resonant frequencies of the pipe from the received acoustic waves comprises filtering the received acoustic waves in an f-k domain to generate filtered f-k data for each of a plurality of radial distances, the method further comprising: converting the filtered f-k data for each of the plurality of radial distances to filtered time-spatial domain data for each of the plurality of radial distances; and determining the radial distance between the acoustic sensor array and the acoustic source by applying beamforming to the plurality of filtered time-spatial domain data.

Example 10 is a tool comprising: an acoustic sensor array comprising a plurality of acoustic sensors, wherein a selected location on the acoustic sensor array divides the plurality of acoustic sensors into two groups of acoustic sensors; and a controller coupled to the acoustic sensor array, the controller configured to position the selected location of the acoustic sensor array substantially at a depth of an acoustic source in a borehole based on symmetricity of an upper and lower section of a frequency-wavenumber (f-k) transform pattern with respect to a selected wavenumber.

In Example 11, the subject matter of Example 10 optionally includes wherein the selected location divides the plurality of acoustic sensors such that a quantity of a first group of acoustic sensors is equal to a quantity of a second group of acoustic sensors.

In Example 12, the subject matter of any one or more of Examples 10-11 optionally include wherein the plurality of acoustic sensors comprise a plurality of hydrophones.

In Example 13, the subject matter of any one or more of Examples 10-12 optionally include wherein the plurality of acoustic sensors are orientated in a linear array of acoustic sensors.

In Example 14, the subject matter of any one or more of Examples 10-13 optionally include wherein the controller is further to determine a radial distance between the acoustic sensor array and the acoustic source by filtering, from acoustic waves received by the plurality of acoustic sensors, resonant frequencies of a pipe.

In Example 15, the subject matter of Example 14 optionally includes wherein the controller is further to filter the received acoustic waves in an f-k domain to generate filtered f-k data and determine the radial distance in response to a largest total energy, of a plurality of total energies, associated with the radial distance, wherein each of the plurality of total energies is associated with a different radial distance and is determined from the filtered f-k data.

In Example 16. the subject matter of any one or more of Examples 14-15 optionally include wherein the controller filters the resonant frequencies of the pipe from the received acoustic waves in an f-k domain to generate filtered f-k data for each of a plurality of radial distances, converts the filtered f-k data for each of the plurality of radial distances to filtered time-spatial domain data for each of the plurality of radial distances, and determines the radial distance between the acoustic sensor array and the acoustic source by applying beamforming to the plurality of filtered time-spatial domain data.

Example 17 is a system comprising: a downhole tool including an acoustic tool, the acoustic tool comprising a plurality of acoustic sensors divided into equal groups of acoustic sensors by an approximate center location between the groups of acoustic sensors; and a controller coupled to the downhole tool, the controller to axially locate the center location with respect to a downhole acoustic source in response to a symmetricity of received acoustic waves from the downhole acoustic source, the controller further to determine a radial distance of the downhole tool from the acoustic source based on a theoretical f-k domain transform pattern used as a mask to filter measured data in the f-k domain.

In Example 18, the subject matter of Example 17 optionally includes wherein the acoustic tool is disposed in a wireline tool.

In Example 19, the subject matter of any one or more of Examples 17-18 optionally include wherein the acoustic tool is disposed in a drill string.

In Example 20, the subject matter of any one or more of Examples 17-19 optionally include wherein the controller is configured to determine the depth and radial distance relative to a fluid flow.

Although specific examples have been illustrated and described herein, it will be appreciated by those of ordinary skill in the art that any arrangement that is calculated to achieve the same purpose may be substituted for the specific examples shown. Various examples use permutations and/or combinations of examples described herein. It is to be understood that the above description is intended to be illustrative, and not restrictive, and that the phraseology or terminology employed herein is for the purpose of description. Combinations of the above examples and other examples will be apparent to those of skill in the art upon studying the above description.

What is claimed is:

1. A method comprising:
   receiving, with an acoustic sensor array having a plurality of acoustic sensors, acoustic waves from an acoustic source located at a depth in a borehole; and
   axially positioning a selected location of the acoustic sensor array substantially at the depth based on a symmetricity, with respect to a selected wavenumber, of an upper and lower section of a frequency-wavenumber (f-k) transform pattern of the received acoustic waves.

2. The method of claim 1, wherein the selected location is substantially at a center location of the acoustic sensor array such that the plurality of acoustic sensors are divided into two equal groups of sensors by the selected location.

3. The method of claim 1, wherein positioning the selected location of the acoustic sensor array comprises determining when the f-k transform pattern of the received acoustic waves is symmetrical with respect to the selected wave number.

4. The method of claim 3, wherein the selected wavenumber is zero.

5. The method of claim 1, wherein positioning the selected location of the acoustic sensor array comprises determining a received total energy from each of the plurality of acoustic sensors in response to performing a Discrete Fourier Transform on the acoustic waves received by each of the plurality of acoustic sensors.

6. The method of claim 1, further comprising determining a radial distance between the acoustic sensor array and the acoustic source.

7. The method of claim 6, wherein determining the radial distance comprises filtering, from the received acoustic waves, resonant frequencies of a pipe.

8. The method of claim 7, wherein filtering the resonant frequencies of the pipe from the received acoustic waves comprises filtering the received acoustic waves in an f-k domain to generate filtered f-k data, the method further comprising:
   determining the radial distance in response to a largest total energy, of a plurality of total energies, associated with the radial distance, wherein each of the plurality of total energies is associated with a different radial distance and is determined from the filtered f-k data.

9. The method of claim 7, wherein filtering the resonant frequencies of the pipe from the received acoustic waves comprises filtering the received acoustic waves in an f-k domain to generate filtered f-k data for each of a plurality of radial distances, the method further comprising:
   converting the filtered f-k data for each of the plurality of radial distances to filtered time-spatial domain data for each of the plurality of radial distances; and
   determining the radial distance between the acoustic sensor array and the acoustic source by applying beamforming to the plurality of filtered time-spatial domain data.

10. A tool comprising:
    an acoustic sensor array comprising a plurality of acoustic sensors, wherein a selected location on the acoustic sensor array divides the plurality of acoustic sensors into two groups of acoustic sensors; and
    a controller coupled to the acoustic sensor array, the controller configured to position the selected location of the acoustic sensor array substantially at a depth of an acoustic source in a borehole based on symmetricity of an upper and lower section of a frequency-wavenumber (f-k) transform pattern with respect to a selected wavenumber.

11. The tool of claim 10, wherein the selected location divides the plurality of acoustic sensors such that a quantity of a first group of acoustic sensors is equal to a quantity of a second group of acoustic sensors.

12. The tool of claim 10, wherein the plurality of acoustic sensors comprise a plurality of hydrophones.

13. The tool of claim 10, wherein the plurality of acoustic sensors are orientated in a linear array of acoustic sensors.

14. The tool of claim 10, wherein the controller is further to determine a radial distance between the acoustic sensor array and the acoustic source by filtering, from acoustic waves received by the plurality of acoustic sensors, resonant frequencies of a pipe.

15. The tool of claim 14, wherein the controller is further to filter the received acoustic waves in an f-k domain to generate filtered f-k data and determine the radial distance in response to a largest total energy, of a plurality of total energies, associated with the radial distance, wherein each of the plurality of total energies is associated with a different radial distance and is determined from the filtered f-k data.

16. The tool of claim 14, wherein the controller filters the resonant frequencies of the pipe from the received acoustic waves in an f-k domain to generate filtered f-k data for each of a plurality of radial distances, converts the filtered f-k data for each of the plurality of radial distances to filtered time-spatial domain data for each of the plurality of radial distances, and determines the radial distance between the acoustic sensor array and the acoustic source by applying beamforming to the plurality of filtered time-spatial domain data.

17. A system comprising:
a downhole tool including an acoustic tool, the acoustic tool comprising a plurality of acoustic sensors divided into equal groups of acoustic sensors by an approximate center location between the groups of acoustic sensors; and
a controller coupled to the downhole tool, the controller to axially locate the center location with respect to a downhole acoustic source in response to a symmetricity of received acoustic waves from the downhole acoustic source, the controller further to determine a radial distance of the downhole tool from the acoustic source based on a theoretical f-k domain transform pattern used as a mask to filter measured data in the f-k domain.

18. The system of claim 17, wherein the acoustic tool is disposed in a wireline tool.

19. The system of claim 17, wherein the acoustic tool is disposed in a drill string.

20. The system of claim 17, wherein the controller is configured to determine the depth and radial distance relative to a fluid flow.

* * * * *